US00PP25209P2

(12) United States Plant Patent
Ulrich et al.

(10) Patent No.: US PP25,209 P2
(45) Date of Patent: Jan. 6, 2015

(54) ***HYDRANGEA* PLANT NAMED 'MONMAR'**

(50) Latin Name: *Hydrangea macrophylla*
Varietal Denomination: Monmar

(76) Inventors: Marc Ulrich, South Pasadena, CA (US); Marcella Ulrich, South Pasadena, CA (US)

( * ) Notice: Subject to any disclaimer, the term of this patent is extended or adjusted under 35 U.S.C. 154(b) by 440 days.

(21) Appl. No.: 13/385,753

(22) Filed: Mar. 5, 2012

(51) Int. Cl.
*A01H 5/00* (2006.01)

(52) U.S. Cl.
USPC ..... Plt./250

(58) Field of Classification Search
CPC ..... A01H 5/02; A01H 5/00; A01H 1/02
USPC ..... Plt./250
See application file for complete search history.

*Primary Examiner* — June Hwu
(74) *Attorney, Agent, or Firm* — C. A. Whealy

(57) ABSTRACT

A new and distinct cultivar of *Hydrangea* plant named 'Monmar', characterized by its upright and somewhat outwardly spreading plant habit; vigorous growth habit; strong dark purple-colored stems; freely and remontant flowering habit with numerous sterile flowers per inflorescence; and large inflorescences with pink-colored flowers.

1 Drawing Sheet

Botanical designation: *Hydrangea macrophylla.*
Cultivar denomination: 'MONMAR'.

BACKGROUND OF THE INVENTION

The present invention relates to a new and distinct cultivar of *Hydrangea* plant, botanically known as *Hydrangea macrophylla* and hereinafter referred to by the name 'Monmar'.

The new *Hydrangea* plant is a naturally-occurring branch mutation of *Hydrangea macrophylla* 'Bailmer', disclosed in U.S. Plant Pat. No. 15,298. The new *Hydrangea* plant was discovered and selected by the Inventor on a single flowering plant of 'Bailmer' in a controlled outdoor environment in Pasadena, Calif. in June, 2007.

Asexual reproduction of the new *Hydrangea* plant by vegetative cuttings in a controlled environment in Visalia, Calif. since May 21, 2010 has shown that the unique features of this new *Hydrangea* plant are stable and reproduced true to type in successive generations.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Monmar'. These characteristics in combination distinguish 'Monmar' as a new and distinct *Hydrangea* plant:

1. Upright and somewhat outwardly spreading plant habit.
2. Vigorous growth habit.
3. Strong dark purple-colored stems.
4. Freely and remontant flowering habit with numerous sterile flowers per inflorescence.
5. Large inflorescences with pink-colored flowers.

Plants of the new *Hydrangea* can be compared to plants of the parent, 'Bailmer'. Plants of the new *Hydrangea* differ from plants of 'Bailmer' primarily in stem color as plants of 'Bailmer' have green-colored stems.

Plants of the new *Hydrangea* can be compared to plants of the *Hydrangea macrophylla* 'Monred', not patented. Plants of the new *Hydrangea* differ from plants of 'Monred' in the following characteristics:

1. Plants of the new *Hydrangea* and 'Monred' differ in stem color as plants of 'Monred' have green-colored stems.
2. Plants of the new *Hydrangea* have a remontant flowering habit whereas plants of 'Monred' do not have a remontant flowering habit.

Plants of the new *Hydrangea* can also be compared to plants of the *Hydrangea macrophylla* 'Merritt's Beauty', not patented. Plants of the new *Hydrangea* differ from plants of 'Merritt's Beauty' in the following characteristics:

1. Plants of the new *Hydrangea* and 'Merritt's Beauty' differ in stem color as plants of 'Merritt's Beauty' have green-colored stems.
2. Plants of the new *Hydrangea* have a remontant flowering habit whereas plants of 'Merritt's Beauty' do not have a remontant flowering habit.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph at the top of the sheet comprises a side perspective view of a typical flowering plant of 'Monmar' grown in a container.

The photograph at the bottom of the sheet is a close-up view of a typical flowering plant of 'Monmar'.

DETAILED BOTANICAL DESCRIPTION

Plants used in the aforementioned photographs and in the following description were grown during the spring in fivegallon containers in a polyethylene-covered greenhouse in Visalia, Calif. and under environmental conditions and cultural practices which closely approximate commercial *Hydrangea* production conditions. Plants were not treated with aluminum sulfate. During the production of the plants, day temperatures ranged from 21° C. to 27° C. and night temperatures ranged from 13° C. to 16° C. Plants of the new *Hydrangea* were 18 months old when the photographs and description were taken. In the following description, color references are made to The Royal Horticultural Society Colour Chart, 2007 Edition, except where general terms of ordinary dictionary significance are used.

Botanical description: *Hydrangea macrophylla* 'Monmar'.

Parentage: Naturally-occurring branch mutation of *Hydrangea macrophylla* 'Bailmer', disclosed in U.S. Plant Pat. No. 15,298.

Propagation:

*Type cutting*.—By vegetative cuttings.

*Time to initiate roots, summer*.—About two to three weeks at temperatures of 24° C. to 38° C.

*Time to produce a rooted young plant, summer*.—About 40 to 60 days at temperatures of 24° C. to 38° C.

*Root description*.—Fine, fibrous; white in color.

*Rooting habit*.—Freely branching; dense.

Plant description:

*Plant and growth habit*.—Upright to somewhat outwardly spreading plant habit; rounded in shape; strong and sturdy stems; vigorous growth habit.

*Plant height*.—About 55 cm.

*Plant diameter or area of spread*.—About 58 cm.

Lateral branch description:

*Branching habit*.—Freely branching habit with about twelve lateral branches per plant.

*Length*.—About 52 cm.

*Diameter*.—About 7 mm.

*Internode length*.—About 6.8 cm.

*Stem texture*.—Smooth, glabrous.

*Strength*.—Strong and sturdy.

*Color*.—Close to N186C; developed stems, close to N199C.

Foliage description:

*Arrangement*.—Opposite, simple.

*Length*.—About 17.8 cm.

*Width*.—About 11.5 cm.

*Shape*.—Broadly elliptical.

*Apex*.—Acuminate.

*Base*.—Mostly cuneate, occasionally oblique.

*Margin*.—Serrate.

*Texture, upper and lower surfaces*.—Smooth, glabrous; leathery.

*Venation pattern*.—Pinnate.

*Color*.—Developing leaves, upper surface: Close to N137A. Developing leaves, lower surface: Close to 137B. Fully expanded leaves, upper surface: Close to N137A; Venation, close to 146B. Fully expanded leaves, lower surface: Close to 147B; venation, close to 147C.

*Petiole*.—Length: About 4.2 cm. Diameter: About 4 mm. Texture, upper and lower surfaces: Smooth, glabrous. Color, upper and lower surfaces: Close to 146C.

Flower description:

*Flower type and habit*.—Single four-lobed sterile and small rounded fertile flowers arranged on terminal compound corymbs; corymbs globular in shape; flowers face upright to outwardly.

*Fragrance*.—None detected.

*Natural flowering season*.—Plants of the new *Hydrangea* flower from June until frost in California; flowering remontant.

*Flower longevity*.—Flowers last about three weeks on the plant, flowers persistent.

*Quantity of flowers*.—Freely flowering habit; about 254 sterile and about 64 fertile flowers per corymb.

*Corymb height*.—About 8.5 cm to 9 cm.

*Corymb diameter*.—About 15 cm to 16 cm.

*Sterile flower diameter*.—About 3 cm to 3.5 cm.

*Sterile flower depth* (*height*).—About 4 mm to 7 mm.

*Fertile flower diameter*.—About 4 mm.

*Fertile flower depth* (*height*).—About 5 mm.

*Flower buds, sterile flowers*.—Length: About 6 mm. Diameter: About 6 mm. Shape: Orbicular. Color: Close to 145C.

*Flower buds, fertile flowers*.—Length: About 5 mm. Diameter: About 4 mm. Shape: Orbicular. Color: Close to 84C.

*Petals, fertile flowers only, sterile flowers without petals*.—Quantity and arrangement: About five in a single whorl fused at the base. Length: About 3 mm. Width: About 2.5 mm. Shape: Elliptical. Apex: Broadly acute. Base: Fused. Margin: Entire. Texture, upper and lower surfaces: Smooth, glabrous; velvety. Color: When opening and fully opened, upper surface: Close to N66D. When opening and fully opened, lower surface: Close to 75A.

*Sepals, sterile flowers*.—Quantity and arrangement: About four, occasionally five, in a single whorl; sepals imbricate. Length: About 1.5 cm. Width: About 1.7 cm. Shape: Elliptical. Apex: Broadly acute. Base: Attenuate. Margin: Entire. Texture, upper and lower surfaces: Smooth, glabrous; velvety. Color: When opening, upper surface: Close to 155D; towards the apex, tinged with close to 75D. When opening, lower surface: Close to 76D. Fully opened, upper surface: Close to 75B; towards the base, close to 76D; color becoming closer to 76C to 76D with development and subsequently becoming light yellow green in color. Fully opened, lower surface: Close to 76B; color becoming closer to 76D with development.

*Sepals, fertile flowers*.—Quantity and arrangement: About five in a single whorl; fused at the base. Length: About 1 mm. Width: About 1 mm. Shape: Roughly ovate. Apex: Acute. Base: Fused. Margin: Entire. Texture, upper and lower surfaces: Smooth, glabrous. Color, upper surface: Close to 157C. Color, lower surface: Close to 157A.

*Peduncles*.—Length: About 3.2 cm. Diameter: About 6 mm. Strength: Strong. Texture: Pubescent. Color: Close to N187A.

*Pedicels, sterile flowers*.—Length: About 2.7 cm. Diameter: About 1.5 mm. Strength: Strong. Texture: Pubescent. Color: Close to 60C to 60D.

*Pedicels, fertile flowers*.—Length: About 1.6 cm. Diameter: About 1.5 mm. Strength: Strong. Texture: Pubescent. Color: Close to 60C to 60D.

*Reproductive organs, fertile flowers only; sterile flowers without reproductive organs*.—Stamens: Quantity per flower: About eight to ten. Filament length: About 2 mm. Filament color: Close to 68B. Anther shape:

Oval. Anther length: About 1 mm. Anther color: Close to 158C. Pollen amount: Sparse. Pollen color: Close to 158D. Pistils: Pistil quantity per flower: One. Pistil length: About 5 mm. Stigma shape: Three-parted. Stigma color: Close to NN155C. Style length: About 1 mm. Style color: Close to 68C. Ovary color: Close to 63D.

*Fruits and seeds*.—Fruit and seed development have not been observed on plants of the new *Hydrangea*.

Disease & pest resistance: Under commercial production conditions, plants of the new *Hydrangea* have not been observed to be resistant to pathogens or pests common to *Hydrangea*.

Temperature tolerance: Plants of the new *Hydrangea* have been shown to be tolerant to temperatures ranging from about −26° C. to about 38° C.

It is claimed:

1. A new and distinct *Hydrangea* plant named 'Monmar' as illustrated and described.

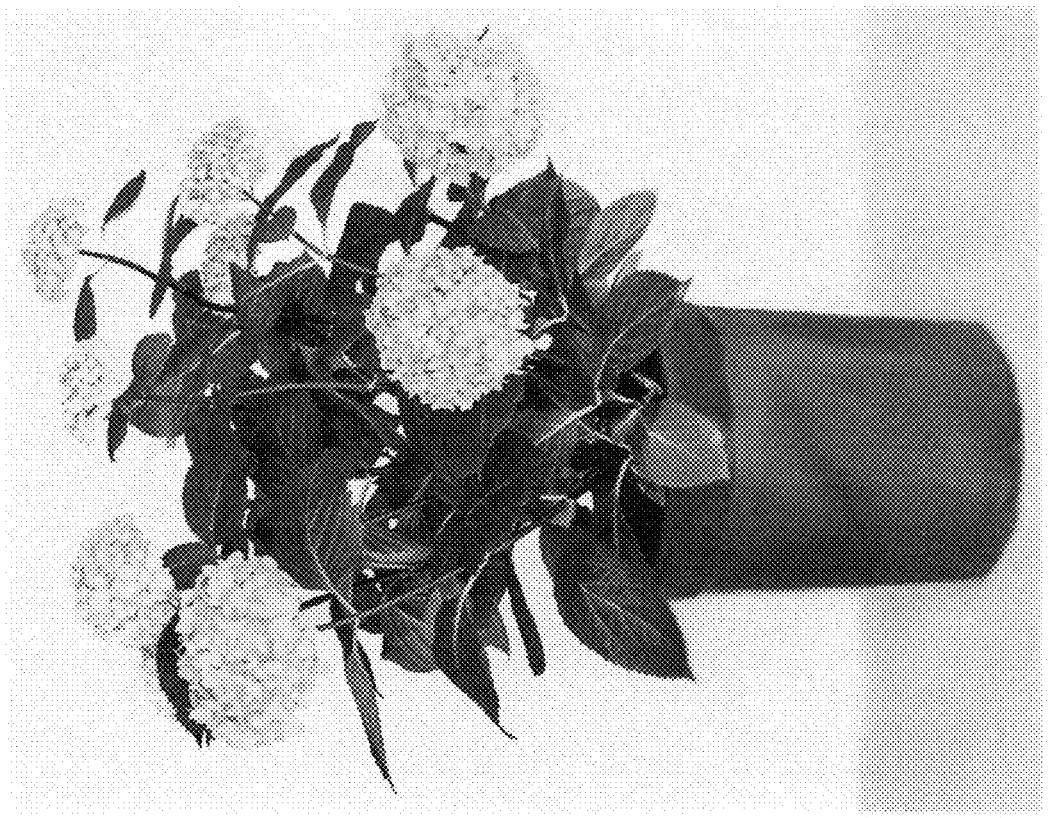
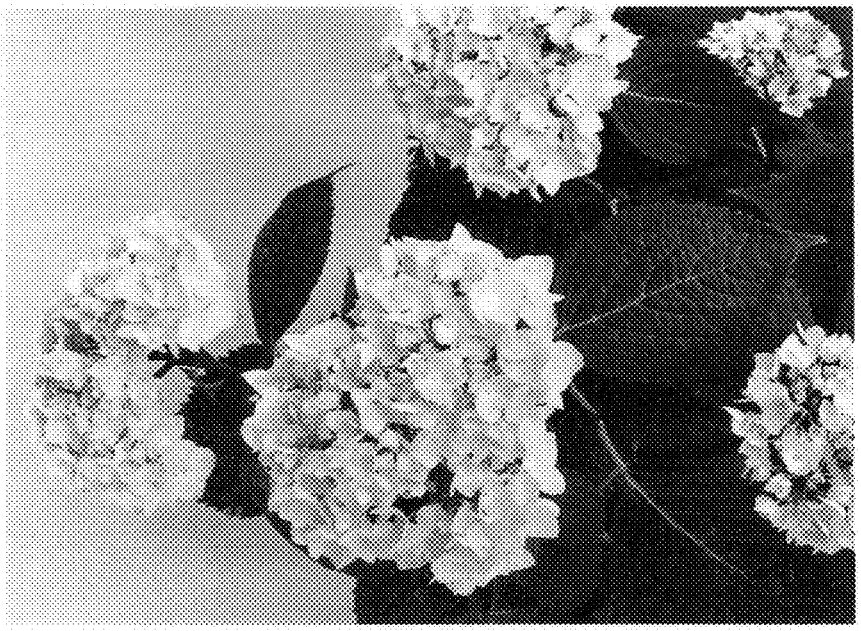

* * * * *